United States Patent [19]

Corley

[11] Patent Number: 5,003,123
[45] Date of Patent: Mar. 26, 1991

[54] PROCESS FOR THE PREPARATION OF CYCLOBUTENOARENES

[75] Inventor: Larry S. Corley, Houston, Tex.

[73] Assignee: Shell Oil Company, Houston, Tex.

[21] Appl. No.: 526,969

[22] Filed: May 17, 1990

Related U.S. Application Data

[63] Continuation of Ser. No. 210,252, Jun. 23, 1988, abandoned.

[51] Int. Cl.$^5$ .............................................. C07C 12/64
[52] U.S. Cl. .................................................... 585/410
[58] Field of Search ........................................ 585/410

[56] References Cited

U.S. PATENT DOCUMENTS

| | | | |
|---|---|---|---|
| 4,540,763 | 9/1985 | Kirchhoff | 526/281 |
| 4,544,782 | 10/1985 | Chapman et al. | 585/443 |
| 4,570,011 | 2/1986 | So | 560/8 |
| 4,851,603 | 7/1989 | Quarderer et al. | 585/410 |

OTHER PUBLICATIONS

Schiess et al, Preparation of Benzocyclobutenes by Flash Vacuum Pyrolysis, *Tetrahedron Letters*, 46, pp. 4569–4572.
Klundt, Benzocyclobutene and It's Derivatives, *Chemical Reviews*, 70, pp. 471–487.
Boekelheide and Ewing, Benzocyclobutenes as Intermediates, *Tetrahedron Letters*, 44, pp. 4245–4248.
Boekelheide, Synthesis and Properties of the [$2_n$] Cyclophanes, *Topics in Current Chemistry*, 113, pp. 100–105.
Gray et al., Synthesis of Benzo [1,2:4,5]dicyclobutene Derivatives, *Journal Americal Chemical Society*, 100, pp. 2892–2893.

*Primary Examiner*—Curtis R. Davis

[57] ABSTRACT

A process is disclosed for the pyrolytic production of a cyclobutenoarene from an o-alkylarylmethyl halide, the process involving the condensation of the pyrolysis product stream in the presence of water vapor. Water can be added to the process with the starting material so that it is present during pyrolysis and/or it can be added to the mixed product stream from the pyrolysis zone. The presence of water vapor in the product stream enables the condensation of aqueous hydrogen halide and provides a relatively simple way to reduce corrosion of downstream equipment.

17 Claims, No Drawings

PROCESS FOR THE PREPARATION OF CYCLOBUTENOARENES

This is a continuation of application Ser. No. 210,252, filed June 23, 1988, now abandoned.

BACKGROUND OF THE INVENTION

This invention relates to a process for preparing cyclobutenoarenes. In a specific aspect, the invention relates to a pyrolytic process for the production of benzocyclobutene.

The four-membered ring of benzocyclobutenes is known to open at elevated temperature to form a very reactive diene which rapidly dimerizes and polymerizes. Molecules containing two or more benzocyclobutene groups are therefore useful as heat-curable thermosetting resins. Also, elastomers or thermoplastics containing benzocyclobutene substitutents crosslink on heating. In order to economically prepare benzocyclobutene-functional resins or polymers, however, an economic method of generating the benzocyclobutene structure itself must be found.

In the past, the benzocyclobutene structure has been synthesized most commonly by the pyrolysis of o-methylbenzyl halides (which may or may not contain additional substituents) at temperatures above 650° C. and pressures below 1 mm Hg. Optionally, an inert diluent is added to enable operation at higher pressures (in the 25 to 200 mm Hg range). With or without an inert diluent, however, the major problem in the reaction is caused by by-product HCl (or other hydrogen halide) formation.

HCl gas tends to corrode the steel used in vacuum pumps. Even if special corrosion-resistant vacuum pumps are used in maintaining the low reaction pressures for flash vacuum pyrolysis, the HCl tends to be absorbed by and to degrade the pump oil, requiring frequent oil changes. The standard way of protecting vacuum pumps from HCl is to pass the gas stream through a packed bed of alkaline material (such as soda lime) upstream from the pump. However, these solid alkaline materials are limited in their ability to absorb acid gases. The alkalies tend to react at the surface with the HCl or other acid gases, with particles of alkali tending to become coated with a layer of halides so that the interior of each particle of alkali remains unreacted. Hence alkali beds must be changed very frequently if used to absorb acid gases formed in stoichiometric amounts in a reaction.

It is therefore an object of the present invention to provide a process for the preparation of cyclobutenoarenes. In one embodiment, it is an object of the invention to provide a relatively non-corrosive pyrolytic process for the preparation of benzocyclobutenes.

SUMMARY OF THE INVENTION

According to the invention, a cyclobutenoarene is prepared by the pyrolysis of an o-alkylarylmethyl halide in a process which involves condensing a mixed product stream from the pyrolysis zone in the presence of water vapor. The water can be added to the process at any point upstream from the condensation zone, including points upstream from the pyrolysis zone, in the pyrolysis reactor, or downstream from the pyrolysis zone. In one embodiment, the invention process involves carrying out the pyrolysis reaction in the presence of water to produce a pyrolysis product mixture comprising a cyclobutenoarene, by-product HX and water vapor, passing the pyrolysis product mixture to a condensation zone wherein product cyclobutenoarene, unreacted starting material and water containing entrained HX are condensed, and recovering the cyclobutenoarene from the condensed organic phase. A substantial amount of the HX by-product can thus be removed from the product mixture without the inconvenience and expense of the use of alkaline beds to remove the major portion of the by-product HX from the product mixture.

DETAILED DESCRIPTION OF THE INVENTION

The invention process involves the pyrolytic conversion of an aromatic starting material to a cyclobutenoarene. The starting material can be an aromatic compound having a methyl halide group ortho to a $C_{1-20}$ alkyl group. The aromatic compound and the $C_{1-20}$ group can contain chemical substituents which, if they are not susceptible to degradation by the pyrolysis conditions, will be present on the product cyclobutenoarene. Examples of suitable o-alkylarylmethyl halide starting materials can be described by formula I below:

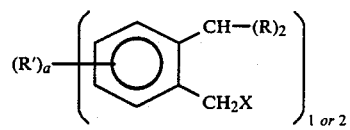

in which X is fluorine, chlorine, bromine or iodine, preferably chlorine or bromine; each R is selected independently from H or substituted or unsubstituted $C_{1-20}$; and each R' is selected independently from H, $C_{1-20}$ alkyl, halide, hydroxyl, cyano, acyl, carbalkoxy, and the like. The benzene ring in formula I can be replaced by a polycyclic ring system, such as naphthalene, anthracene, biphenyl, phenanthrene and the like, or by a heterocyclic ring system, such as pyrrole, thiophene or dibenzofuran, for example. Examples of such aromatic compounds include o-methylbenzyl chloride, o-ethylbenzyl chloride, o-propylbenzyl chloride, 3-methoxy-o-methylbenzyl chloride, methyl 4-methyl-3-chloromethylbenzoate, ethyl 4-butyl-3-chloromethylbenzoate, benzyl 4-propyl-3-chloromethylbenzoate, phenyl 4-butyl-3-bromomethylbenzoate, 2-chloromethyl-3-methylthiophene and 1-chloromethyl-2-methylnaphthalene. The product cyclobutenoarenes can be described by formula II below, in which R, R', a and X are as defined above.

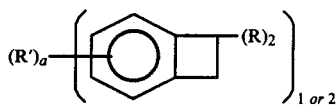

The preferred o-alkylarylmethyl halide, because it is a starting material for the pyrolytic preparation of benzocyclobutene, is o-methylbenzyl chloride,

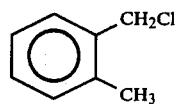

For convenience herein, the process will be described in terms of the preferred embodiment, and the aromatic starting material will therefore be referred to as "o-methylbenzyl chloride" and the pyrolysis product as "benzocyclobutene," but it will be understood that the invention process can be practiced with a wide range of starting materials such as those described above.

In the invention process, the o-methylbenzyl chloride starting material is introduced into a reactor and subjected to pyrolysis conditions, which generally include a temperature at least about 550° C., preferably within the range of about 600° to about 850° C., and a pressure generally (except under modified reaction conditions which can include, for example, the use of an organic reaction solvent) no higher than about 25 mm Hg, generally within the range of about 0.01 to about 10 mm Hg. The starting material is maintained under pyrolysis conditions for a time sufficient for conversion of the starting material to a product mixture containing benzocyclobutene, which generally occurs in less than about 1 second.

The pyrolysis reaction is preferably carried out in the presence of water. The water can be introduced into the vacuum chamber and passed to the pyrolysis reactor as a mixed vapor stream with the o-methylbenzyl chloride starting material or can be introduced directly into the pyrolysis reactor as a separate stream. Introduction of water to the reactor can be carried out in a pre-reaction zone wherein a vessel containing a mixture of starting material and water is heated to evaporate the components, which are then passed to the pyrolysis zone as a mixed vapor stream. One disadvantage to such an approach is that the ratio of starting material to water in the vapor phase is determined by the vapor pressures of the two components at the temperature in the pre-reaction zone, and this ratio may not be the optimum for the process. In an alternate method, water is metered at the desired rate into a heated pre-reaction vessel containing starting material at the desired temperature. In a preferred variation on this method, both water and starting material are metered into a pre-reaction vessel which is maintained at a temperature sufficiently high to evaporate both materials as they enter, providing maximum control of the composition of the vapor passing into the pyrolysis reactor.

The amount of water present in the pyrolysis reactor in the above-described embodiment is preferably an amount effective to suppress tar formation in the pyrolysis zone, generally at least about 6%, preferably within the range of about 10 to about 20%, based on the weight of the o-methylbenzyl chloride starting material.

The pyrolysis reaction can be carried out in the presence or absence of an organic solvent, such as benzene, toluene, xylene, chlorobenzene, nitrobenzene, alkyl benzoates and phenyl acetate, for example. When a solvent is used for the starting material, it is expected that reaction pressures will be higher, generally within the range of about 25 mm Hg to about 200 mm Hg.

A reaction product mixture containing benzocyclobutene, unreacted starting material, by-product HX, where X is the halide from the starting material, and water vapor (if water was present during pyrolysis) is passed from the pyrolysis zone to a condensation zone, preferably via a downstream heated zone wherein water vapor is added to the mixed product stream. Thus, according to a second embodiment of the invention, water is added to the pyrolysis process at a point downstream from the pyrolysis reaction zone. The total amount of water vapor in the mixed product stream passed to the condensation zone will vary depending upon the reaction conditions and the conversion of starting material to cyclobutenoarene, with higher conversion rates calling for greater amounts of water. The amount of water in the mixed product stream can generally be expected to be within the range of about 20 to about 200 weight percent, preferably about 80 to about 125 weight percent, based on the weight of the o-methylbenzyl chloride starting material. Generally, the total water in the mixed product stream passed to the condensation zone will be approximately equal, on a weight basis, to the starting material, and will be generally chosen so as to be equal to or greater than the amount necessary to provide a maximum boiling $H_2O/HCl$ azeotropic mixture. Too little water will result in high acidity of the gas stream passed to the downstream pumps, while an excessive amount of water will result in ice clogging in the condensation zone.

In the condensation zone, the reaction product mixture is cooled in one or more stages of decreasing temperature to a temperature effective for condensation of a product mixture including a liquid organic phase containing benzocyclobutene product, any side products formed, and unreacted starting material, and an aqueous phase containing HX. The organic phase can be separated from the aqueous phase by mechanical means such as draining, and the benzocyclobutene product can be recovered by, for example, distillation to separate benzocyclobutene from unreacted starting material, treatment with $H_2SO_4$ for styrene and phenylacetylene removal, and fractional freezing or selective absorption for o-xylene removal. Any uncondensed vapor, the majority of which will generally comprise hydrogen gas and carbon monoxide, can be passed via the vacuum pumps to vent.

The condensation of HX as aqueous HX in the cold traps between the pyrolysis furnace and the vacuum pumps offers advantages over alternative methods of addressing HX in the product stream, such as avoiding the expense of HX-resistant pumps, permitting the use of smaller vacuum pumps to maintain a given reaction pressure, and eliminating the explosion hazard posed by liquid nitrogen HX traps and the capacity limitations of alkali traps. The presence of water in the pyrolysis zone can have the benefit of suppressing tar formation during pyrolysis.

The process can include other process steps as desired for improving the product yield or process efficiency. Alkaline beds can be positioned upstream from the pumps to neutralize any residual HX in the gaseous product stream.

EXAMPLE 1

This experimental run was performed to prepare benzocyclobutene according to a conventional pyrolysis method in which essentially no water is present in the reactor during the pyrolysis reaction. A pyrolysis apparatus was assembled as follows. A quartz tube approximately 60 mm in diameter and containing semicircular quartz baffles spaced about 100 mm apart along the length of the tube was placed inside a tube furnace. The heated zone of the tube furnace was approximately 600 mm long. At one end of the tube was a heated 1000-mL flask which contained a mixture of 500 g o-methylbenzyl chloride and 25 g EPON® Resin 828 (the latter material added as a stabilizer to prevent Friedel-Crafts condensation reactions from occurring during the batch evaporation 6/17/88). At the other end of the quartz tube was a train of two dry-ice traps leading to a vacuum pump with a 160 liter/minute pumping capacity.

The furnace was heated to 675° C., the liquid in the flask was heated to 40–45° C., and the vacuum pump was turned on at full vacuum (reducing system pressure to about 0.2 mm Hg). The system was maintained under these conditions for approximately 7 hours. At the end of this period, the vacuum was broken and the traps were allowed to warm to room temperature. The two traps contained about 136 grams of organic material (19.4 g/hour). Gas chromatography of the isolated material showed that 61% comprised a peak corresponding to benzocyclobutene in retention time (corresponding to a benzocyclobutene production rate of 11.8 g/hour), with o-methylbenzyl chloride apparently making up most of the remainder of the material. The HCl by-product of the reaction was allowed to pass through the vacuum pump. The vacuum pump was inoperable the following day because of corrosion and had to be repaired.

EXAMPLE 2

The run of Example 1 was repeated except for the addition of a vessel approximately 100 mm in diameter containing about 300 g of soda lime between the two dry ice traps. The system was operated for five hours under conditions similar to those in Example 1. At the end of this period, no pump damage was detectable, but the amount of organic material in the cold traps was only 52 grams (10.4 g/hour). The benzocyclobutene content of the organic phase (by gas chromatography) was 67%, for a benzocyclobutene production rate of only 7 g/hour.

EXAMPLE 3

The run of Example 1 was repeated except that the furnace temperature was increased to 800° C. and water was injected into the feed flask at the rate of approximately one gram per minute. The vacuum pump was turned on and the system was operated for five hours. Even when only enough heat was applied to the feed flask to keep the temperature of its contents at 0°–20° C., the cold traps contained 257.4 grams of organic phase at the end of the run (along with 296 g of aqueous phase). The organic phase contained 39% benzocyclobutene according to gas chromatography, for a benzocyclobutene production rate of 20.2 g/hour. (The increase in furnace temperature was necessary because, with water injection, there was a significant increase in flow rate through the hot tube, so that the organic material in the traps contained only 2% benzocyclobutene if the furnace temperature was 675° C.)

EXAMPLE 4

The system previously used was modified such that both water and o-methylbenzyl chloride were metered continuously into the feed flask. The heating mantle covering the lower portion of the feed flask was kept hot enough to prevent any liquid accumulation in the feed flask. Also, a higher capacity vacuum pump (300 liters/min) was used. The furnace was heated to 900° C., full vacuum was applied, and water and o-methylbenzyl chloride were allowed to flow into the heated feed flask. The system was operated for three hours at a pressure between 0.3 and 0.5 mm Hg. the cold traps were then allowed to warm to room temperature. The cold traps contained 784 grams of organic phase (of which 42% was benzocyclobutene by gas chromatography) and 801 grams of aqueous phase. The net benzocyclobutene production rate was 116.5 g/hour.

I claim:

1. A process for preparing a cyclobutenoarene comprising the steps of
   (a) introducing into a pyrolysis zone a starting material mixture comprising an o-alkylarylmethyl halide and from about 6 to about 20 weight percent water, based on the weight of the o-alkylarylmethyl halide;
   (b) subjecting said starting material mixture to pyrolysis conditions for the o-alkylarylmethyl halide and producing a reaction product mixture comprising a cyclobutenoarene, a hydrogen halide and water vapor;
   (c) passing the reaction product mixture to a condensation zone and producing a condensation product comprising a liquid cyclobutenoarene and an aqueous solution of the hydrogen halide; and
   (d) recovering the cyclobutenoarene.

2. The process of claim 1 in which the o-alkylarylmethyl halide is o-methylbenzyl halide.

3. The process of claim 1 in which the water is added in an amount of at least about 10 weight percent, based on the weight of the o-alkylarylmethyl halide.

4. The process of claim 1 in which the o-alkylarylmethyl halide is o-methylbenzyl chloride and the cyclobutenoarene is benzocyclobutene.

5. The process of claim 4 in which the pyrolysis conditions include a temperature of at least about 550° C. and a pressure less than about 25 mm Hg.

6. The process of claim 4 in which the o-alkylarylmethyl halide and water are heated to a vapor state upstream from the pyrolysis zone and are introduced into the pyrolysis zone as a mixed vapor stream.

7. The process of claim 4 in which the water is added in an amount within the range of from about 10 to about 20 weight percent, based on the weight of the o-methylbenzyl chloride.

8. The process of claim 4 in which the pyrolysis conditions include a temperature within the range of about 600 to about 850° C. and a pressure within the range of about 0.01 to about 10 mm Hg.

9. The process of claim 8 which further comprises the step of adding water to the reaction product mixture downstream from the pyrolysis zone.

10. A process for preparing a cyclobutenoarene comprising the steps of:
    (a) introducing into a pyrolysis zone an o-alkylarylmethyl halide;
    (b) subjecting the o-alkylarylmethyl halide to pyrolysis conditions for a time sufficient to produce a pyrolysis product comprising a cyclobutenoarene and a hydrogen halide;
    (c) adding water vapor to the pyrolysis product downstream from the pyrolysis zone;
    (d) passing the pyrolysis product and water vapor to a condensation zone and subjecting the pyrolysis product and water to condensation conditions effective to condense liquid cyclobutenoarene and a water solution of the hydrogen halide; and
    (e) recovering the cyclobutenoarene.

11. The process of claim 10 in which the water is added in an amount within the range of about 20 to about 200 weight percent, based on the weight of the o-alkylarylmethyl halide.

12. The process of claim 10 in which the water is added in an amount within the range of from about 80 to about 125 weight percent, based on the weight of the o-alkylarylmethyl halide.

13. The process of claim 10 in which the o-alkylarylmethyl halide is o-methylbenzyl chloride and the cyclobutenoarene is benzocyclobutene.

14. The process of claim 10 in which the pyrolysis conditions include a temperature of at least about 550° C. and a pressure less than about 25 mm Hg.

15. The process of claim 13 in which the water is added downstream from the pyrolysis zone in an amount within the range of about 20 to about 200 weight percent, based on the weight of the o-alkylarylmethyl halide.

16. The process of claim 13 in which the pyrolysis conditions include a temperature within the range of about 600° to about 850° C. and a pressure within the range of about 0.01 to about 10 mm Hg.

17. The process of claim 1 in which the pyrolysis reaction is carried out in an organic solvent.

* * * * *